United States Patent [19]

Kirschenheuter et al.

[11] Patent Number: 5,240,956
[45] Date of Patent: Aug. 31, 1993

[54] ESTER INHIBITORS

[75] Inventors: Gary P. Kirschenheuter, Arvada, Colo.; Raymond T. Cunningham, Houston, Tex.; John C. Cheronis, Lakewood, Colo.

[73] Assignee: Cortech, Inc., Denver, Colo.

[21] Appl. No.: 866,301

[22] Filed: Apr. 13, 1992

Related U.S. Application Data

[63] Continuation of Ser. No. 610,207, Nov. 7, 1990, abandoned.

[51] Int. Cl.$^5$ .................. A61K 31/40; C07D 209/12; C07D 207/30

[52] U.S. Cl. .................. 514/419; 514/415; 514/427; 514/428; 548/494; 548/572

[58] Field of Search .................. 548/494, 462, 572; 514/415, 427, 428, 419

[56] References Cited

FOREIGN PATENT DOCUMENTS

0079623 5/1983 European Pat. Off. ............ 548/562

Primary Examiner—John M. Ford
Assistant Examiner—Y. N. Gupta

[57] ABSTRACT

2-Heteroaromatic alkanoate esters which are useful as inhibitors of human leukocyate or neutrophil elastase.

4 Claims, 3 Drawing Sheets

ESTER INHIBITORS

This is a continuation of application Ser. No. 07/610,207, filed on Nov. 7, 1990, which was abandoned upon the filing hereof.

The present invention relates to certain oxidant sensitive and insensitive 2-heteroaromatic alkanoate esters which are useful as inhibitors of human leukocyte elastase (HLE) or equivalently human neutrophil elastase (HNE).

RELATED APPLICATION

This application is related to the commonly assigned U.S. application Ser. No. 07/528,967, filed May 22, 1990.

BACKGROUND OF THE INVENTION

There has been considerable research effort in recent years toward the development of HLE or HNE inhibitors because it appears that HLE or HNE may be responsible for a variety of human diseases. Tests have shown that there is an apparent association between HLE and emphysema. See, for example, in Sandbero et al., *The New England Journal of Medicine*, 304:566 (1981). Other diseases and medical problems, such as arthritis and related inflammatory conditions, dermatitis and ischemia/reperfusion injury have also been associated with HLE. See, Dinerman et al., *JACC*, Vol. 15, No. 7, June 1990:1559-63. Accordingly, there is a need for compounds which are effective to inhibit HLE or HNE.

Typical prior efforts to deal with elastase inhibition are disclosed in the patent literature, for instance, U.S. Pat. Nos. 4,683,241 and 4,801,610.

SUMMARY OF THE INVENTION

The principal object of the present invention is to provide certain new compounds which are useful as elastase inhibitors. These compounds are characterized by their relatively low molecular weight and high selectivity with respect to HLE. As a consequence, they can be used to prevent, alleviate or otherwise treat disease characterized by the degradation effects caused by HLE on connective tissues in mammals, including humans.

The compounds of the invention may be structurally illustrated by the following formula (I):

wherein:

$R_1$ and $R_2$, which may be the same or different, are selected from the group consisting of:

hydrogen, alkyl of 1-6 carbons, cycloalkyl of 3 to 6 carbons or together represent a methylene group —(CH$_2$)$_n$— where n is a whole number of from 1 to 6;

Ar is an optionally substituted phenyl group; and

HET is a heterocyclic ring containing one or more N, S or O atoms in the ring.

The optional substitution on the Ar phenyl group may comprise from one to five substituents selected from hydrogen, halogen, nitro, —C(O)CH$_3$, S(O)$_p$R$_9$ where p is 0, 1 or 2 and R$_9$ is hydroxy, —ONa or optionally substituted alkyl of 1-12 carbons or optionally substituted cycloalkyl including, for example, lower alkyl substituted with halogen (such as trifluoromethyl) or lower alkyl bearing a carboxylic acid group, especially —CH$_2$C(CH$_3$)$_2$COOH. Preferably, however, the Ar phenyl is substituted with —SCH$_3$, —S(O)CH$_3$ or —S(O)$_2$CH$_3$.

The Het substituent is advantageously selected from the group consisting of the following:

furanyl benzofuranyl thienyl pyrrolyl or benzpyrrolyl where $R^3$ is hydrogen or lower alkyl. Other heterocyclic groups include, for example, benzthienyl, imidazolyl, pyraxolyl, triaxolyl, pyridyl, pyrimidyl or the like.

The Het group may itself by substituted by, for example, hydrogen, halogen, haloalkyl of 1-12 carbons (e.g. trifluoromethyl), alkyl of 1-12 carbons, cycloalkyl of 3-7 carbons, alkoxy of 1-12 carbons, alkenyl of 2-12 carbons, phenyl, naphthyl or benzyl.

It will be appreciated that when $R_1$ and $R_2$ are different, the carbon atom to which these substituents are attached (i.e. the "alpha carbon") is a chiral center and the resulting compounds may exist in enantiomerically pure form or as racemic mixtures of the enantiomers. The invention contemplates such mixtures (+/−) as well as the separate (+or −) enantiomers thereof.

Non-toxic pharmaceutically acceptable salts of the indicated compounds are also contemplated.

PREFERRED EMBODIMENTS OF THE INVENTION

Particularly advantageous for present purposes are the compounds of formula (I) where one of R. and R, is hydrogen and the other is alkyl, particularly ethyl; Ar is phenyl substituted in the position ortho or para to the —O— linkage by SCH$_3$, S(O)CH$_3$,S(O)$_2$CH$_3$ or NO$_2$ and HET is furanyl, benzofuranyl, thienyl or pyrrolyl joined to the rest of the molecule through a ring carbon ortho or meta to the heterocyclic O, S or N atom.

As a further feature of the invention, it has been found that compounds which have been modified so as to remove the chiral center at the alpha carbon, i.e. by making $R_1$ and $R_2$ the same, e.g. either methyl or ethyl, or by merging $R_1$ and $R_2$ into a cycloalkyl ring (such as cyclopropyl, cyclobutyl, cyclopentyl or cyclohexyl) are particularly advantageous for use as human neutrophil elastase inhibitors.

According to another aspect of the invention, it has been found that compounds wherein the Ar phenyl has a —SCH$_3$ substituent in the ortho or para positions, or where the Ar phenyl includes a —S—CH$_2$C(CH$_3$)$_2$COOH substituent in the para position, are particularly useful. These compounds appear to be oxidatively activatable as in vivo inhibitors, i.e. the —S— (sulfide) group seems to be oxidized in situ to the sulfoxide —S(O)- or to the sulfone —S(O)$_2$—. In this regard, it has been found that the potency of the compounds where Ar is substituted by —S— (sulfide), —S(O)— (sulfoxide) or S(O)$_2$— (sulfone) increases in the series as follows: is substituted by —S— (sulfide), —S(O)— (sulfoxide) or —S(O)$_2$— (sulfone) increases in the series as follows:

—S— < —S(O)— < —S(O)$_2$—

Consequently, it appears that the potency of the —S— compounds can be increased by oxidants present at the site of HLE mediated damage to form the corresponding sulfoxides or sulfones.

Representative compounds according to the invention are disclosed in Table I using the following formula for purposes of exemplification:

| Compound | HET | R$^1$ | R$^2$ | R$^4$ |
|---|---|---|---|---|
| 1 | furyl (O) | H | C$_2$H$_5$ | SCH$_3$ |
| 2 | " | H | C$_2$H$_5$ | S(O)CH$_3$ |
| 3 | " | H | C$_2$H$_5$ | S(O)$_2$CH$_3$ |
| 4 | benzofuryl | H | C$_2$H$_5$ | SCH$_3$ |
| 5 | " | H | C$_2$H$_5$ | S(O)CH$_3$ |
| 6 | " | H | C$_2$H$_5$ | S(O)$_2$CH$_3$ |
| 7 | thienyl (S) | H | C$_2$H$_5$ | SCH$_3$ |
| 8 | " | H | C$_2$H$_5$ | S(O)CH$_3$ |
| 9 | " | H | C$_2$H$_5$ | S(O)$_2$CH$_3$ |
| 10 | " | H | C$_2$H$_5$ | NO$_2$ |
| 11 | thienyl (S) | H | C$_2$H$_5$ | SCH$_3$ |
| 12 | " | H | C$_2$H$_5$ | S(O)CH$_3$ |
| 13 | " | H | C$_2$H$_5$ | S(O)$_2$CH$_3$ |
| 14 | " | H | C$_2$H$_5$ | NO$_2$ |
| 15 | pyrrolyl (NH) | H | C$_2$H$_5$ | SCH$_3$ |
| 16 | " | H | C$_2$H$_5$ | S(O)CH$_3$ |
| 17 | " | H | C$_2$H$_5$ | S(O)$_2$CH$_3$ |
| 18 | " | H | C$_2$H$_5$ | NO$_2$ |
| 19 | " | H | C$_2$H$_5$ | SCH$_2$C(CH$_3$)$_2$COOH |
| 20 | " | H | C$_2$H$_5$ | S(O)CH$_2$C(CH$_3$)$_2$COOH |

| Compound | HET | R¹ | R² | R⁴ |
|---|---|---|---|---|
| 21 | (indole) | H | C₂H₅ | SCH₃ |
| 22 | " | H | C₂H₅ | S(O)CH₃ |

The products of the invention may be prepared by procedures available and known to those in the art. Representative synthesis methods are illustrated in the accompanying FIGS. 1, 2 and 3 comprising, respectively, Reaction Scheme A, Reaction Scheme A (continued) and Reaction Scheme B detailed hereinafter.

Figure 1:
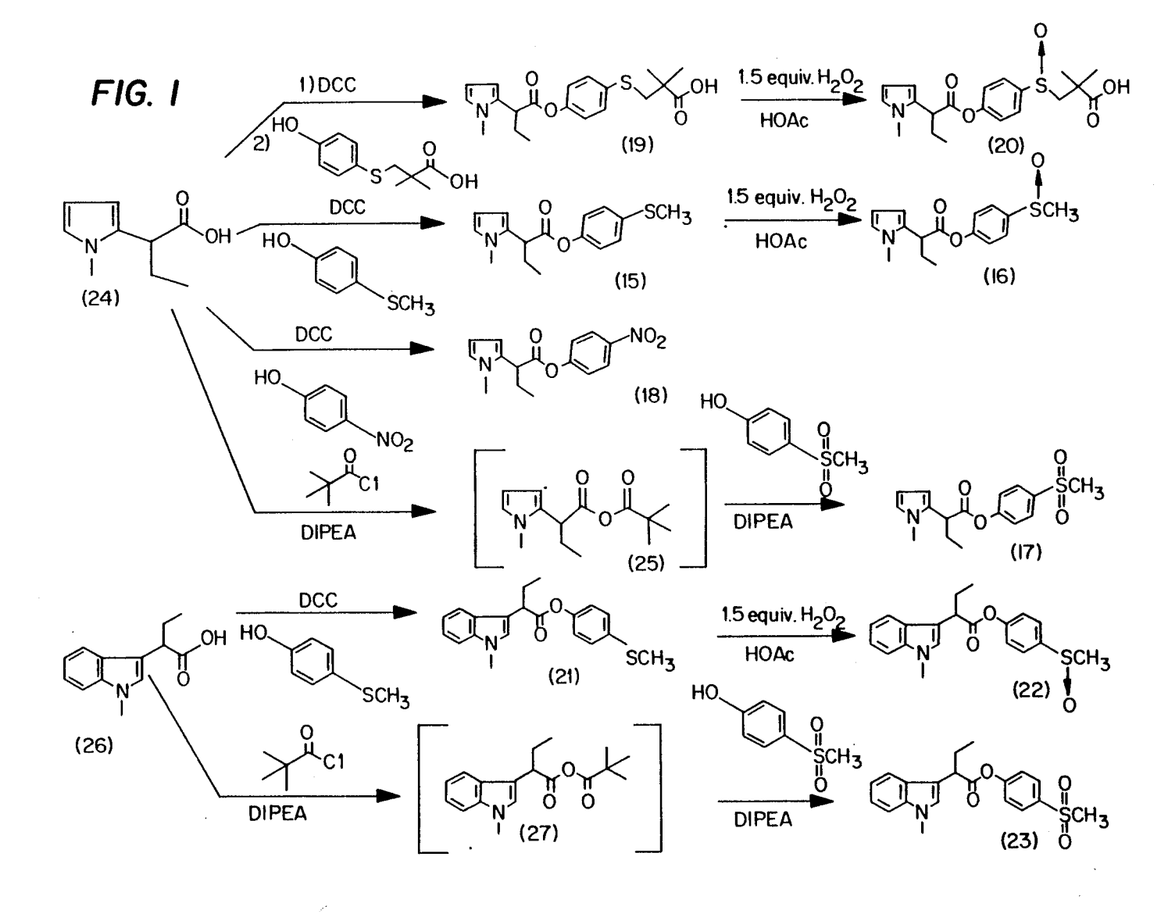
Figure 2:
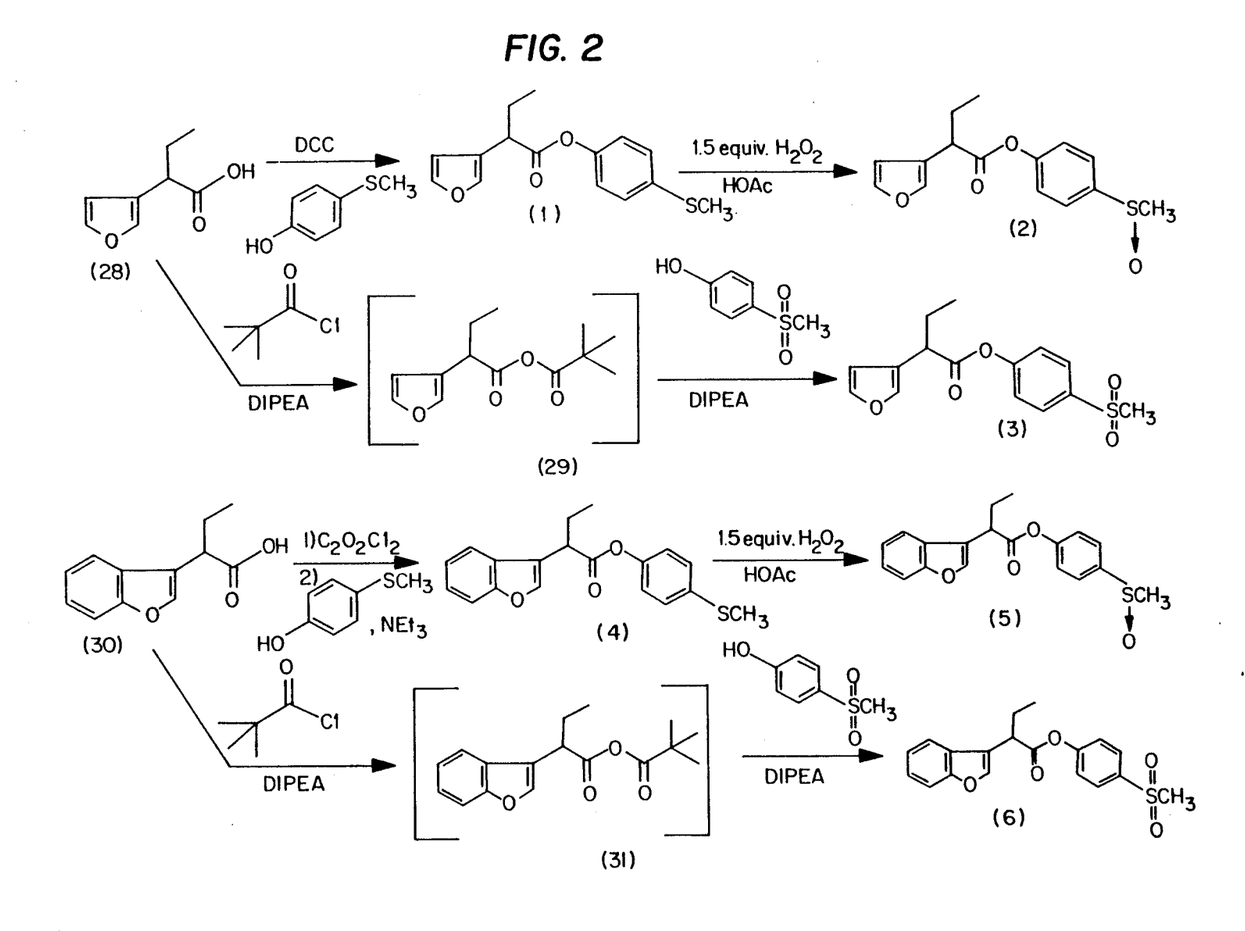
Figure 3:
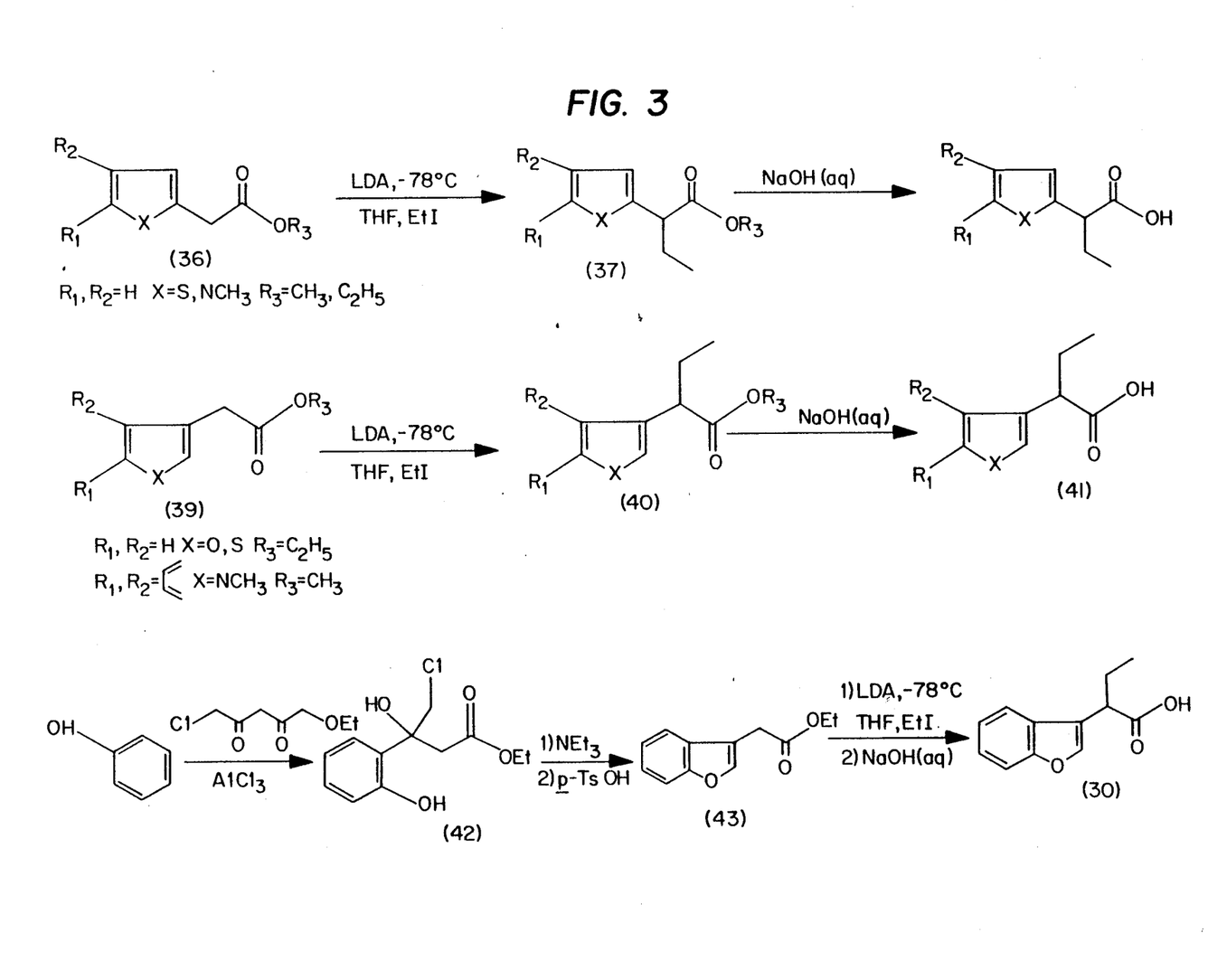

The synthesis of the various substituted esters may be achieved by the use of three general techniques. The first approach utilizes dialkylcarbodiimides such as dicyclohexylcarbodiimide (DCC) to form nascent symmetrical anhydrides from the carboxylic acid starting material. The symmetrical anhydrides may be allowed to form prior to addition of the phenolic component as illustrated in the synthesis of compound (19) or may be formed in situ in the presence of the phenolic compound whereupon the ester is produced directly as in the formation of compounds (1), (15), (18) and (21). The second esterification method proceeds via the acid chloride which is obtained upon treatment of the carboxylic acid with oxalyl chloride. Subsequent reaction of the acid chloride intermediates with the appropriate phenol in the presence of a base such as triethylamine affords the desired esters in high yields. This method found application in the synthesis of the thiophene analogs (7), (10), (11) and (14) as well as the benzofuran derivative (4). Finally, the third procedure involves treatment of the starting carboxylic acid with pivaloyl chloride in the presence of diisopropylethylamine (DIPEA) to give the unsymmetrical anhydrides (for example (25), (27), (29) and (31)) followed by addition of 4-methylsulfonylphenol which is acylated to form the esters (3), (6), (17) and (23). There exist additional methods in the literature of synthetic chemistry by Which esters of the type described above may be synthesized. These additional methods are evident to practitioners skilled in the art.

The esters such as (1), (4), (7), (11), (15), (19) and (21) which contain a thioether moiety may be oxidized with 1.5 equivalents of hydrogen peroxide in acetic acid to the corresponding sulfoxide derivatives (2), (5), (8), (12), (16), (20) and (22). Furthermore, the thiophene sulfides (7) and (11) may be converted to the sulfones (9) and (13) by treatment with excess hydrogen peroxide in acetic acid for 24–48 hours.

The 2-substituted butyric acids (24), (26), (28), (30), (32) and (34) are obtained readily by alkylation of the corresponding substituted acetates (36) and (39) followed by base hydrolysis as depicted in Reaction Scheme B. The 3-benzofuranacetate (43) was obtained in high yield by condensation of phenol with ethyl 4-chloro-3-oxobutyrate to give (42) which was cyclized with triethylamine and dehydrated with p-toluene sulfonic acid. Additional methods of synthesizing these precursors are known to those skilled in the art.

The following examples are given to illustrate the preparation of specific compounds according to the invention:

EXAMPLE 1

Synthesis of 4-Methylmercaptophenyl 2-(1-Methyl-2-pyrrole)butyrate (15)

(A) Methyl 2-(1-Methyl-2-pyrrole)butyrate

A solution of lithium diisopropylamide (253 mmol) THF was prepared under $N_2$ and cooled to $-78°$ C. Methyl 2-(1-methyl-2-pyrrole)acetate (36.85 g, 241 mmol) was added dropwise with stirring followed by 32 mL of HMPA. The reaction mixture was stirred for 30 minutes and iodoethane (19.2 ml, 241 mmol) was added dropwise over 15 minutes. The cooling bath was removed and the reaction mixture was allowed to warm to room temperature. After 2 hours the reaction mixture was quenched with $H_2O$ and extracted with ether. The combined organic layers were washed with water, dried over anhydrous $MgSO_4$ and concentrated. The residue was distilled under vacuum (0.14 mm, 80° C.) to afford the product as a pale yellow oil (37.0 g, 85%). $^1$H NMR (CDCl$_3$)δ0.961 (t, 3H, J =7.4 Hz), 1.80–1.95 (m, 1H), 2.05–2.20 (m, 1H), 3.53 (t, 1H, J =7.65 Hz), (m, 2H), 6.55–6.56 (m, 1H); $^{13}$C NMR (CDCl$_3$)δ11.94, 25.01, 33.60, 44.78, 51.75, 106.6, 107.0, 122.3, 130.1, 173.8.

(B) 2-(1-Methyl-2-pyrrole)butyric Acid

A mixture of methyl 2-(1-methyl-2-pyrrole)butyrate (37.0 g, 204 mmol) and 250 mL of 2.5 M aqueous NaOH was heated under reflux for 3 hours. The reaction mixture was cooled to room temperature, acidified to pH=1.0 and extracted with ether. The ether layer was dried over anhydrous MgSO. and concentrated to give 28.9 g (87%) of the desired product. $^1$H NMR (CDCl$_3$) δ0.992 (t, 3H, J=7.35 Hz), 1.80–1.95 (m, 1H), 2.04–2.20 (m, 1H), 3.52 (t, 1H, J =7.65 HZ), 3.60 (s, 3H), 6.09-6.11 (m, 2H), 6.56–6.58 (m, 1H), 12.24 (br s, IH, —OH); $^{13}$C NMR (CDCl$_3$) δ11.94, 24.68, 33.63, 44.65, 106.9, 107.2, 122.6, 129.3, 180.2.

(C) Methylmercaptophenyl 2-(Methyl-2-pyrrole)butyrate (15)

Dicyclohexycarbodiimide (44.0 g, 216 mmol) was added to a stirred solution of 2-(1-methyl-2-pyrrole)-butyric acid (28.5 g, 176 mmol) and 4-methylmercaptophenol (23.7 g, 165 mmol) in 500 mL of dry dichloromethane. After 16 hours acetic acid (120 mL) was added, the solution filtered and the filtrate concentrated under vacuum. The residue was dissolved in ether and treated with anhydrous potassium carbonate until neutral. The mixture was filtered and the filtrate washed with 5% NaOH, dried over anhydrous MgSO. and concentrated under vacuum. The residue was distilled under vacuum (0.7 mm, 185° C.) to afford 24.6 g (49%) of the product (15). $^1$H NMR (CDCl$_3$) δ1.06 (t, 3H, J=7.5 Hz), 1.88-2.03 (m, lH), 2.15-2.30 (m, IH), 2.45 (s, 3H), 3.66 (s, 3H), 3.74 (t, 1H, J=7.65 Hz), 6.10-6.18 (m, 2H), 6.59-6.62 (m, lH), 6.95 (d, 2H, J=8.40 Hz). 7.24 (d, 2H, J=8.40 Hz); $^{13}$C NMR (CDCl$_3$) δ11.97, 16.18, 25.21, 33.76, 44.94, 107.0, 122.0, 122.6, 128.1, 129.5, 135.8, 148.7, 171.8.

EXAMPLE 2

Synthesis of 4-Methylsulfinylohenyl 2-(1-Methyl-2-pyrrole)butyrate (16)

Hydrogen peroxide (16.2 mL of a 30% solution) was added to a stirred mixture of 4-methylmercaptophenyl 2-(1-methyl-2-pyrrole)butyrate (24.6 g, 86.5 mmol) in 120 mL
of glacial acetic acid. After 1 hour 120 mL of H,O was added and the mixture extracted with ether. The organic layer was washed with water and dried over anhydrous potassium carbonate overnight. The solution was filtered and concentrated to afford the product sulfoxide (16) as a white solid. Trituration of the crude solid with ether gave 21.0 g (81%) of the pure product as white crystals. $^1$H NMR (CDCl$_3$) δ1.07 (t, 3H, J=7.5 Hz), 2.90-2.05 (m, 1H), 2.16-2.31 (m, IH), 2.70 (s, 3H), 3.67 (s, 3H), 3.78 (t, 1H, J=7.50 Hz), 6.11-6.18 (m, 2H), 6.59-6.61 (m, lH),
7.20 (d, 2H, J=8.70 Hz), 7.63 (d, 2H, J=8.70 Hz); $^{13}$C NMR (CDCl$_3$) 11.89, 25.16, 33.70, 43.86, 44,84, 107.0, 107.3, 122.7(2X), 124.9, 129.0, 143.0, 153.0, 171.3.

EXAMPLE 3

Synthesis of 4-Methylsulfonylphenyl 2-(1-Methyl-2-pvrrole)butvrate (17)

Trimethylacetylchloride (1.14 g, 9.5 mmol) was added to a solution of 2-(1-methyl-2-pyrrole)butyric acid (1.58 g, 9.5 mmol) and diisopropylethylamine (1.23 g, 9.5 mmol) in 20 mL of dichloromethane. After stirring for 1 hour, a solution of 4-methylsulfonylphenol (133 g, 9.5 mmol) and diisopropylethylamine (1.23 g, 9.5 mmol) in 15 mL of dichloromethane was added and the reaction mixture was stirred at room temperature overnight. The reaction
mixture was washed with H$_2$O (4×20 mL), dried over anhydrous MgSO and concentrated. The residue was chromatographed on flash silica gel (ethyl acetate/hexane, 1:4) to afford 1.30 g (43%) of the product (17). $^1$H NMR (CDCl$_3$) δ1.07 (t, 3H, J=7.35 Hz), 1.92-2.07 (m, lH), 2.17-2.32 (m, IH), 3.04 (s, 3H), 3.69 (s, 3H), 3.79 (t, 1H, J=7.65 Hz), 6.11-6.19 (m, 2H), 6.60-6.65 (m, lH), 7.24 (d, 2H, J=8.70 Hz), 7.95 (d, 2H, J=8.70 Hz); C NMR (CDCl$_3$) δ11.90, 25.21, 33.75, 44.42, 44.89, 107.2, 107.4, 122.6, 122.8, 128.8, 129.3, 138.0, 155.1, 172.0.

EXAMPLE 4

Synthesis of 4-(2'-Carboxy-2'-methylpropylmercaoto)phenyl 2-(1-Methyl-2-pyrrole)butvrate (19)

Dicyclohexylcarbodiimide (1.05 g, 5.1 mmol) was added to a solution of 2-(1-methyl-2-pyrrole)butyric acid (1.74 g, 10.4 mmol) and a catalytic amount of 4-dimethylaminopyridine in 20 mL of dry THF. After stirring for 1 hour, a solution of 2,2-dimethyl-3-(4'-hydroxyphenylthio)propionic acid (1.5 g, 5.1 mmol) in 20 mL of dry THF was added and the mixture was allowed to stir overnight. The reaction mixture was concentrated, the residue dissolved in ether and acetic acid (2 mL) was added. The dicyclohexylurea by-product was filtered off and the filtrate was washed with dilute NaHCO, (3×20 mL). The organic layer was dried over anhydrous MgSO. and concentrated. Residual acetic acid was removed by adding cyclohexane and distilling the azeotrope to give 0.64 g (33%) of the ester (19). $^1$H NMR (CDCl$_3$)δ1.08 (t, 3H, J=7.20 Hz), 1.30 (s, 6H), 1.90 4 2.05 (m, lH), 2.15-2.30 (m, 1H), 3.16 (br s, 2H), 3.67 (s, 3H), 3.75 (t, 1H, J=7.50 Hz), 6.10-6.17 (m, 2H), 6.60-6.65 (m, 1H), 6.95 (d, 2H, J =8.40 Hz), 7.39 (d, 2H, J=8.40 Hz), 10.6 (br s, 1H,—OH); $^{13}$C NMR (CDCl$_3$) δ12.01, 24.35, 25.23, 33.80, 43.76, 45.02, 52.78, 107.0, 107.3, 122.1, 122.7, 129.4, 131.7, 134.4, 149.7, 171.7, 182.9.

EXAMPLE 5

Synthesis of 4-(2'-Carboxy-2-methylpropylsulfinyl)phenyl 2-(1-Methyl-2-pyrrole)butvrate (20)

To a stirred solution of 4-(2'-carboxy-2'-methylpropylmercapto)phenyl 2-(1-methyl-2-pyrrole)butyrate (0.5I g, 1.36 mmol) in 5 mL of glacial acetic acid was added 0.23 mL of 30% hydrogen peroxide. The reaction mixture was allowed to react for 35 minutes and was quenched with 15 mL of H$_2$O. The resulting solution was extracted with ether and the organic layer was separated and dried over anhydrous MgSO$_4$. The product was obtained upon evaporation of the solvent to provide 0.44 g (82%) of material. $^1$H NMR (CDCl$_3$) δ1.07 (t, 3H, J=7.35 Hz), 1.43 (s, 3H), 1.53 (s, 3H), 1.90-2.05 (m, 1H), 2.15-2.30 (m, 1H), 3.0-3.15 (m, 2H). 3.67 (s, 3H), 3.77 (t, 1H, J=7.65 Hz), 6.10-6.20 (m, 2H), 6.60-6.62 (m, 1H), 7.20 (d, 2H, J =8.40 Hz), 7.71 (d, 2H, J=8.70 Hz), 10.6 (br s, lH, OH); $^{13}$C NMR (CDCl$_3$) δ1.99, 24.68, 25.24, 25.64, 33.81, 41.73, 44.90, 68.81, 107.1, 107.3, 122.8 (2X), 125.6, 129.1, 144.4, 153.1, 171.4, 180.2.

EXAMPLE 6

Synthesis of 4-Methylmercaotoohenyl 2-(3-thiophene)butvrate (11)

Oxalyl chloride (13.7 mL of a 2.0M solution, 27.4 mmol) was added to a solution of 2-(3-thiophene)-butyric acid (3.90 g, 22.9 mmol) in 25 mL of dry dichloromethane and the resulting reaction mixture stirred for 3 hours. 15 The volatiles were removed under vacuum and the residue dissolved in a sufficient amount of dichloromethane to give a 0.33 M solution of the acid chloride. This acid chloride solution (45.5 mL, 15 mmol) was added to a mixture of 4-methylmercaptophenol (1.80 g, 15 mmol) and triethylamine (1.52 g, 15 mmol) in 15 mL of dry dichloromethane. After stirring overnight, the precipitated solids were filtered off and the filtrate washed with 1 M Na,CO,. The product 2.55 g (72%) was isolated by concentration of the organic layer and chromatography of the residue on silica gel. NMR (CDCl$_3$) δ1.05 (t, 3H, J=7.23 Hz), 1.89-2.04 (m, 1H), 2.15-2.30 (m, lH), 2.48 (s, 3H), 3.87 (t, lH, J=7.70 Hz), 6.99 (d, 2H, J=8.49 Hz), 7.18 (d, 1H, J=4.98 HZ), 7.27 (d, 1H, J=2.58 Hz), 7.38 (d, 2H, J=2.58 Hz), 7.38

Hz); $^{13}$C NMR (CDCl$_3$) δ11.78, 16.19, 26.47, 48.64, 122.0, 122.2, 126.0, 127.2, 128.1, 135.8, 138.8, 148.7, 172.4.

EXAMPLE 7

Synthesis of 4-Methylsulfinylohenyl 2-(3-thioohene)butvrate (12)

Hydrogen peroxide (9.048 mL of a 30% solution, 4.1 mmol) was added to stirred solution of 4-methylmercaptophenyl 2-(3-thiophene)butyrate (0.80 g, 2.7 mmol) in 8 mL of glacial acetic acid. After 1 hour, ether was added and the resulting solution was washed with HO (3 ×15 mL) and then saturated NaHCO$_3$ (3×15 mL). The organic layer was dried over anhydrous K$_2$CO$_3$ and evaporated to yield 0.69 g (83%) of the desired product sulfoxide b 2.05 (m, 1H) 2.14–2.29 (m, 1H), 2.71 (s, 3H), 3.88 (t, 1H, J=7.62 Hz), 7.15 (d, 1H, J=4.92 Hz), 7.21 (d, 2H, J=8.61 Hz), 7.25 (d, 1H, J=3.06 Hz), 7.35 (dd, 1H, J=4.95 Hz), 7.65 (d, 2H, J=8.64 Hz); $^{13}$C NMR (CDCl$_3$)δ11.77, 26.38, 43.93, 48.93, 48.63, 122.7, 125.0, 126.2, 127.1, 138.4, 143.1, 153.0, 172.1.

EXAMPLE 8

Synthesis of 4-Methylsulfonylohenyl 1-(3-thiophene)butvrate (13)

A mixture of 4-methylmercaptophenyl 2-(3-thiophene)butyrate (0.90 g. 3.0 mmol), glacial acetic acid (3 mL) and 30% hydrogen peroxide (3 mL) were stirred together for 3 days. The reaction mixture was poured onto cracked ice and extracted with ether. The organic layer was washed with H,O, dried over anhydrous K$_2$CO$_3$ and concentrated to yield 0.21 g (21%) of the sulfonyl derivative (13). $^1$H NMR (CDCl$_3$) δ1.02 (t, 3H, J=7.35 Hz), 1.88–2.03 (m, 1H), 2.16–2.31 (m, 1H), 3.04 (s, 3H), 3.90 (t, 1H, J=7.68 Hz), 7.15 (d, 1H, J=5.01 Hz), 7.22–7.27 (m, 1H), 7.25 (d, 2H, J=8.55 Hz), 7.96 (d, 2H, J= 8.67 C NMR (CDCl$_3$) δ11.68, 26.25, 44.33, 48.51, 122.4, 122.6, 126.3, 127.0, 129.2, 138.0, 154.9, 171.7.

As noted earlier, the present compounds demonstrate HLE inhibiting activity which indicates that these compounds would be useful in the treatment of such diseases as emphysema, arthritis, artheriosclerosis or the like. For such uses, the compounds would be administered by the usual route, e.g. orally, intravenously, subcutaneously, intraperitoneally or intramuscularly. For emphysema, the compounds would be administered in therapeutically effective amounts, usually orally or rectally, or as a mist for bronchial inhalation.

The amount of compound used to inhibit HLE will vary with the nature and extent of the condition involved. It is contemplated, for example, that mists containing from 0.05 to 20% of the active compound with dosages in the order of 2–100 mg per dosage unit several times a day would provide a therapeutically effective amount for the treatment of emphysema. Variations and adjustments in the size and frequency of administration can be determined to provide the desired HLE inhibition.

Pharmaceutical compositions containing the active compounds of the invention may comprise tablets, capsules, solutions or suspensions with c,onventional nontoxic pharmaceutically acceptable carriers. These compositions may include the usual types of additives, e.g. disintegrating or suspending agents or the like. Compounds selected for intravenous use should be soluble in aqueous solutions, while those used in, for example, oral formulations need not be water-soluble. Topical formulations are also contemplated for use in the treatment of, for example, dermatitis and acne.

The compounds of the invention are extremely potent and highly selective inhibitors of neutrophil elastase. The compounds also appear to show adequate serum stability. The water solubility of the compounds varies and it will be appreciated that the ultimate mode of administration for each compound will depend, at least to some extent, on the solubility of the compound involved.

Without intending to be limited to any theory of operation or function, it appears that the compounds of the invention bind to the active site of neutrophil elastase. More particularly, it appears that the acyl group binds to the S substrate position, i.e. the valine or proline-valine region of the binding pocket and the phenolic group extends into the S' positions.

The following tests have been used to determine the activity of the compounds of the present invention:

Potency (I$_{50}$ Determination)

Reagents:
A) 0.075M sodium phosphate, 20% dimethyl sulfoxide (DMSO), pH 7.7=substrate and inhibitor buffer
B) 0.075M sodium phosphate, no DMSO, pH 7.7 inhibitor buffer
C) 10 mM human neutrophil elastase (HNE) substrate =N-methoxysuccinyl-ala-ala-pro-val-pNA in DMSO
0.01M sodium acetate, 20% DMSO, pH 5.5 =enzyme buffer (dilution)
E) 0.01M sodium acetate, pH 5.5—enzyme buffer (storage)
F) HNE (1 mg) dissolved in 1 ML of reagent E for storage at −20° C.

Make a 10 mM stock of the inhibitor in DMSO. Dilute an aliquot (10 μL) up to 1.0 mL in reagent A (100 M). Serially dilute 100 μL of the 100 μM stock to 10.1, 1.0, 0.1, 0.01 μM in reagent A. Apply 100 μL of the diluted material to the wells of a 96-well plate. Dilute an aliquot of reagent F 1:150 in reagent D, apply 50 μL aliquots to the indicated wells and incubate for 7 minutes at room temperature.

The HNE substrate solution is made by taking 100 μL of reagent C into 500 μL of reagent A and 400 μL of reagent B. After the 7 minutes of incubation, the substrate (50 μL) is applied to each well. The HNE catalyzed reaction is then monitored spectrophotometrically at 405 nm using an ELISA plate reader machine (UVMAX, Molecular Devices) which processes the raw data with an on-board kinetics program. The enzyme activity is plotted against different inhibitor concentrations and the I$_{50}$ value is determined by using a curve fitting software program. Once the "screening" I$_{50}$ has been approximated, a more precise I=value can be obtained by examination of inhibitor concentrations around this value.

Specificity Determination

Reagents:
1) Porcine Pancreatic Elastase (PPE) 1 mg/mL in 0.01M sodium acetate, pH 5.5. An aliquot of this stock solution is diluted 1:20 in 0.01M sodium acetate, 20% DMSO, 10 mM CaCl$_2$, pH 5.5.
2) α- Chymotrypsin (αCH) 1 mg/mL in 0.01 M sodium acetate, pH 5.5. An aliquot of this stock is diluted 1:85 in 0.01M sodium acetate, 20% DMSO, 10 mM CaCl$_2$, pH 5.5, 0.005% triton X-100 detergent.

3) PPE substrate: N-succinyl-ala-ala-ala-pNA 20 mM stock in DMSO.

α-CH substrate: N-succinyl-ala-ala-pro-leu-pNA- 20 mM stock in DMSO.

Inhibitor, substrate buffer: 0.1 M tris-HCl, 0.01 M CaCl$_2$, 0.005% triton X-100, 20% DMSO, pH 7.7.

I$_{50}$ determinations for the compounds of Table I are set forth in Table II:

TABLE II

| Compound | I$_{50}$ (μM) |
| --- | --- |
| 1 | 6.06 |
| 2 | 1.44 |
| 3 | 0.47 |
| 4 | 3.80 |
| 5 | 0.42 |
| 6 | 0.15 |
| 7 | 3.00 |
| 8 | 0.43 |
| 9 | 0.29 |
| 10 | 0.27 |
| 11 | 1.50 |
| 12 | 0.13 |
| 13 | 0.05 |
| 14 | 0.12 |
| 15 | 6.20 |
| 16 | 0.46 |
| 17 | 0.06 |
| 18 | 0.20 |
| 19 | 0.20 |
| 20 | 0.50 |
| 21 | 33.0 |
| 22 | 1.9 |

It will be noted that the compounds where R$^4$ is —SCH$_3$ have significantly higher I$_{50}$'s in each comparative instance.

Experiments have been conducted on dogs to study the effect of the compounds of the invention in the treatment of ischemia reperfusion injuries. These experiments indicated that, when using compound No. 16 as illustrative of the present compounds, a significant reduction in infarct size was obtained in the animals treated with compound No. 16 when compared to the controls.

The protocol used in the experiment referred to in the preceding paragraph involved the following:

Male mongrel dogs (13 to 17 kg) were anesthetized with sodium pentobarbital, 30 mg/kg i.v., intubated and ventilated with room air via a Harvard respirator. Lead II of the electrocardiogram and hemodynamics were monitored continuously throughout the course of the experiment. A catheter was inserted into the left carotid artery and advanced into the left ventricle for the continuous recording of left ventricular pressure. A second catheter was inserted into the right femoral artery for measurements of arterial blood pressure. A left thoracotomy was performed at the fifth intercostal space, the heart was suspended in a pericardial cradle, and the left circumflex coronary artery (LCX) was isolated distal to its atrial branch and proximal to any major ventricular branches. An electromagnetic flow probe was placed on the artery for the determination of basal LCX blood flow. Initially, the LCX was constricted partially with a ligature to an extent that does not change resting flow, but the peak flow increment (reactive hyperemic response) after a 10 sec complete occlusion was decreased by at least 70% (critical stenosis). After 15 min of partial constriction, the LCX was occluded completely with a second ligature. Total occlusion was maintained for 90 min, followed by 24 hr of reperfusion with the critical stenosis in place for the initial 30 min of reperfusion. The critical stenosis limited the reperfusion hyperemia and therefore reduced the severity of reperfusion arrhythmias, the extent of hemorrhagic myocardial infarcts, and the potential for ventricular fibrillation. Upon restoration of regional perfusion, the arterial, venous and atrial cannulae was removed, the thoracotomy incision was closed in layers, the wound dressed and the animal returned to the postoperative recovery facility. After 24 hr of reperfusion, the animal was reanesthetized, the thoracotomy incision opened, the heart fibrillated electrically and removed rapidly for postmortem quantification of infarct size.

Animals were randomized to receive either the test compound or a placebo (diluent) administered as an intracoronary infusion via a catheter inserted into the left circumflex coronary artery just distal to the point at which the vessel is occluded. The dose was determined on the basis of known pharmacokinetic data and the infusion was maintained throughout the 90 period of regional ischemia as well as during the 24 hour reperfusion period. The administration of test compound or placebo was infused beginning 60 minutes before occlusion of the left circumflex coronary artery.

Regional myocardial blood flow was determined with tracer-labelled microspheres (15 μm diameter) by the reference withdrawal method. Two injections of microspheres were made in each experiment with the order of the isotopes being randomized. Reference arterial blood samples were obtained simultaneously from both the femoral and carotid arteries at a constant rate with a Harvard withdrawal pump, beginning immediately before the injection of microspheres into the left atrium and ending 2 minutes later. The reference sample counts were averaged for calculation of myocardial blood flow. If the reference sample counts varied by more than 15%, the data were discarded. Each bottle of microspheres was placed in an ultrasonic bath with subsequent vortex agitation before injection to assure that adequate dispersal of the microspheres suspensions was achieved before being injected.

Regional myocardial blood flow was determined 10 minutes before reperfusion of the left circumflex coronary artery. A second determination of regional myocardial blood flow was made 10 minutes before termination of the study (5 hours and 50 minutes after reperfusion). Tissue samples weighing 0.5–1.0 grams were dissected from the subepicardial, midmyocardial and subendocardial regions of the heart in the regions perfused by the left circumflex coronary artery and by the left anterior descending coronary artery, representing the myocardium at risk and the non-involved myocardial regions respectively. At least 3 sections from each heart were used so that blood flows to each region represented the average of 3 to 4 samples for each experiment.

The size of myocardial infarction was determined with an ex vivo dual-perfusion staining technique. Cannulae were inserted into the aorta above the coronary ostia and into the LCX at the site of the previous occlusion. The LCX bed was perfused with 1.5% triphenyl tetrazolium hydrochloride (TTC.) in 20 mM potassium phosphate buffer (pH 7.4, 38° C.). The aorta was perfused in a retrograde manner with 0.25% Evan's blue dye. Both the LCX region and the remainder of the heart were perfused with their respective stains at a constant pressure of 100 mm Hg for 10 min. The heart was put into six equal sections approximately 1.0 cm thick perpendicular to the apical-basal axis. The staining technique readily delineated the area of left ventricle at risk of infarction and infarcted myocardium within the area at risk from the area of left ventricle that is not dependent on the LCX for blood flow and that is stained with Evan's blue dye. Viable myocardium within the area at risk was stained red due to the conversion of the colorless TTC to a red formazan precipitate by tissue dehydrogenase enzymes. Infarcted myocardium within the area at risk remained unstained due to the loss of dehydrogenase enzymes from the irreversibly injured tissue. The transverse ventricular sections were trimmed of right ventricular muscle and valvular and fatty tissue and then traced onto a clear plastic overlay for the planimetric determination of the size of infarction. Infarct size was expressed as a percent of the area at risk and as a percent of the total left ventricle.

All data obtained were expressed as the mean±SEM. Paired or group test analyses were applied where appropriate. Differences were considered significant for $p \leq 0.05$. When comparisons among more than two means were made (infarct/area at risk, infarct/left ventricle, area at risk/left ventricle), the data were compared by analysis of variance and Scheffe's multiple comparison confidence intervals.

Both myocardial area at risk and collateral blood flow are important determinants in the extent of ischemic myocardial necrosis. Infarct size was assessed in relation to collateral blood flow measured in the inner two thirds of the central ischemic zone. An analysis of covariance was performed, in which collateral blood flow was the independent variable, with the object of determining if there existed a statistically significant difference in the calculated infarct size between the two groups when the influence of collateral blood flow is controlled.

The average results obtained numerically represented as the infarct size were as follows based on tests with 10 dogs in each category:

| Placebo | Compound No. 16 |
|---|---|
| 52.79 + SEM 4.9 | 40.59 + SEM 4.2 |

As noted earlier, these results show that infarct size is considerably reduced by using a compound according to the invention.

It will be appreciated that various modifications may be made in the invention described herein without departing from the spirit and scope of the invention as defined in the following claims wherein:

We claim:

1. A compound of the formula:

wherein:

$R_1$ is hydrogen and $R_2$ is ethyl;

Ar is phenyl substituted with a $SCH_3$, $S(O)CH_3$, $S(O)_2CH_3$, $SCH_2C(CH_3)_2COOH$, $S(O)CH_2C(CH)_3)_2COOH$, $S(O)_2CH_2C(CH)_3(CH_3)_3)_2COOH$ or $NO_2$ substituent; and HET is a heterocyclic ring of the formula:

where $R^3$ is hydrogen or lower alkyl.

2. A compound according to claim 1 of the formula:

wherein HET is th epyrroly ring, $Rp^1$ is hydrogen, $R^2$ is ethyl and $R^4$ is $-SCH_3$, $-S(O)CH_3$ or $-S(O)_2CH_3$.

3. A pharmaceutical composition for inhibiting undesired elastase activity comprising an effective amount of a compound according to claim 1 and a carrier therefor.

4. A method of inhibiting undesired elastase activity which comprises administering to a subject in need of such inhibition, an effective amount of a compound according to claim 1.

* * * * *